US00PP13423P3

(12) United States Plant Patent
Ishikawa

(10) Patent No.: US PP13,423 P3
(45) Date of Patent: Dec. 24, 2002

(54) HYBRID TEA ROSE PLANT NAMED 'KEIHATAKAHO'

(75) Inventor: Takashige Ishikawa, Aichi-Ken (JP)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/832,840

(22) Filed: Apr. 12, 2001

(65) Prior Publication Data

US 2002/0007504 P1 Jan. 17, 2002

(30) Foreign Application Priority Data

Jul. 6, 2000 (JP) ..... 12635

(51) Int. Cl.[7] ..... A01H 5/00
(52) U.S. Cl. ..... Plt./137
(58) Field of Search ..... Plt./137, 136, 130

*Primary Examiner*—Bruce R. Campell
*Assistant Examiner*—June Hwu
(74) *Attorney, Agent, or Firm*—Burns, Doane, Swecker & Mathis, LLP

(57) ABSTRACT

A new and distinct variety of Hybrid Tea rose plant is provided which abundantly forms attractive deep pink blossoms. The blossoms commonly possess approximately 50 petals each. The buds are large and are borne on straight erect stems. Attractive dark green semi-glossy foliage is formed. The new variety is particularly well suited for forming cut flowers under greenhouse growing conditions.

1 Drawing Sheet

BOTANICAL/COMMERCIAL CLASSIFICATION

*Rosa hygrida*/Hybrid Tea Rose Plant.

VARIETAL DENOMINATION

'Keihatakaho'.

SUMMARY OF THE INVENTION

The new variety of *Rosa hybrida* Hybrid Tea rose plant of the present invention was discovered during 1998 in Japan while growing among plants of the 'Febesa' variety (U.S. Plant Pat. No. 11,529). The new variety of the present invention accordingly is believed to be a naturally-occurring mutation of the 'Febesa' variety of unknown causation.

The new variety was selected and preserved primarily because of its distinctive blossom coloration that differed from the parent 'Febesa' variety. More specifically, the 'Febesa' variety exhibits blossoms that are light pink in coloration whereas the new variety of the present invention forms blossoms that are a deeper pink in coloration. In addition, the number of petals per blossom is different. More specifically, the 'Febesa' variety commonly forms approximately 20 to 24 petals per blossom on average whereas the new variety of the present invention commonly exhibits approximately 50 petals per blossom on average.

It was found that the new variety of Hybrid Tea rose plant of the present invention possesses the following combination of characteristics:

(a) forms attractive large buds on straight erect stems, (b) forms in abundance deep pink blossoms, (c) forms attractive dark green semi-glossy foliage, and (d) is particularly well suited for the production of cut flowers under greenhouse growing conditions.

The new variety well meets the needs of the horticultural industry and can be used to advantage during the commercial production of cut flowers under greenhouse growing conditions.

The new variety of the present invention also can be distinguished from the 'Keihayanasa' variety (U.S. Plant patent application Ser. No. 09/832,834 filed concurrently herewith) that also is a mutation of the 'Febesa' variety. More specifically, the 'Keihayanasa' variety forms salmon pink blossoms having approximately 30 to 34 petals per blossom.

The new variety of the present invention has been found to undergo asexual propagation by a number of routes, including budding, grafting, and the rooting of cuttings. Such asexual propagation by the above-mentioned methods as performed in France has shown that the characteristics of the new variety are strictly transmissible by such asexual propagation from one generation to another.

The new variety has been named the 'Keihatakaho' variety.

BRIEF DESCRIPTION OF THE PHOTOGRAPH

The accompanying photograph shows as nearly true as it is reasonably possible to make the same, in a color illustration of this character, typical specimens of the flower of the new variety wherein the bud is shown together with flowers in various stages of opening. The depicted plant was being grown in a greenhouse at Chiba-Ken, Japan during May.

DETAILED DESCRIPTION

The chart used in the identification of the colors is The R.H.S. Colour Chart of The Royal Horticultural Society, London, England. The terminology which precedes reference to the chart has been added to indicate the corresponding color in more common terms. The description is based on the observation of two year-old specimens of the new variety during April while on *Rosa indica* understock and growing in greenhouses at Le Cannet des Maures, Var, France.

Class: Hybrid Tea.

Plant:

*Height*.—When pruned to height of 85 cm, floral stems having a length of approximately 50 to 80 cm commonly are produced at the end of the growing season.

*Habit*.—Erect.

Branches:

*Color*.—Young stems: Yellow Green Group 146A, and bear tiny prickles. Adult wood: Green Group 137A, and bear some prickles.

*Thorns*.—Size: Medium, and approximately 1 cm in length. Quantity: Numerous. Color: Greyed-Orange Group 167A, and near Greyed-Orange Group 167D when young.

Leaves:

*Stipules*.—Adnate, pectinate, narrow, near Yellow-Green Group 147D in coloration, approximately 0.5 cm in width and approximately 1.5 cm in length.

*Petioles*.—Near Yellow-Green Group 147A to 147D, and somewhat glandular.

*Leaflets*.—Number: 3, 5 and 7 (most often). Shape: elliptic. Serration: Regular. Texture: Smooth and glabrous. General appearance: Very dense, dark green and semi-glossy foliage. Color (young foliage): Upper surface: Near Yellow-Green Group 147A. Under surface: Near Yellow-Green Group 147B. Color (adult foliage): Upper surface: Near Green Group 139A. Under surface: Near Green Group 138A.

Inflorescence:

*Number of flowers*.—Commonly one per stem.

*Peduncle*.—Glandular, bear a few tiny prickles, strong, near Green Group 138B and the length is approximately 8.5 cm on average.

*Sepals*.—Tomentous on the upper surface, smooth on the under surface, approximately 3.5 cm in length, near Green Group 137D in coloration and with some extensions as illustrated in the photograph.

*Buds*.—Shape: Elongated. Size: Large. Length: Approximately 5.5 cm on average.

*Flower*.—Shape: Commonly with a high center. Diameter: Approximately 9 cm on average. Color (when opening begins): Upper surface: Deep pink, near Red-Purple Group 65A to 65C. Under surface: Deep pink, near Red-Purple Group 65B to 65C. Color (when blooming): Upper surface: Deep pink, near Red-Purple Group 65A to 65C. Under surface: Deep pink, near Red-Purple Group 65B to 65C. Color (at end of opening): Upper surface: Deep pink, near Red-Purple Group 65A to 65C. Under surface: Deep pink, near Red-Purple Group 65B to 65C. Color (spot at petal base): Upper surface: Near Yellow Group 2C. Under surface: Near Yellow Group 2D. Fragrance: None. Lasting quality: Excellent when cut and placed in a vase with the blossoms commonly lasting approximately 15 days. Petal shape: Rounded apex with an obtuse base and relexed edges. Petal size: Approximately 4 cm on average in length and width during July. Petal number: Approximately 50 on average. Petaloids: None observed. Petal drop: The petals commonly detach cleanly. Stamen number: Approximately 106 on average. Anthers: Near Yellow-Orange Group 18B and approximately 0.3 cm in size. Filaments: Near Yellow-Orange Group 16D and approximately 1 cm in length. Pollen: Ochre in coloration. Pistil number: Approximately 146 on average. Stigmas: Near Yellow-Orange Group 18D and approximately 0.1 cm in width. Styles: Near Greyed-Purple Group 184C and approximately 1 cm in length on average. Receptacle: Near Green Group 138B in coloration, smooth, approximately 1 cm in diameter, and in longitudinal section in the shape of funnel. Hips: None observed.

Development:

*Vegetation*.—Very vigorous.

*Blooming*.—Very abundant.

*Resistance to diseases*.—Excellent especiallly with respect to Powdery Mildew, and Black Spot.

I claim:

1. A new and distinct variety of Hybrid Tea rose plant characterized by the following combination of characteristics:

(a) forms attractive large buds on straight erect stems, (b) forms in abundance attractive deep pink blossoms, (c) forms attractive dark green semi-glossy foliage, and (d) is particularly well suited for the production of cut flowers under greenhouse growing conditions;

substantially as herein shown and described.

* * * * *

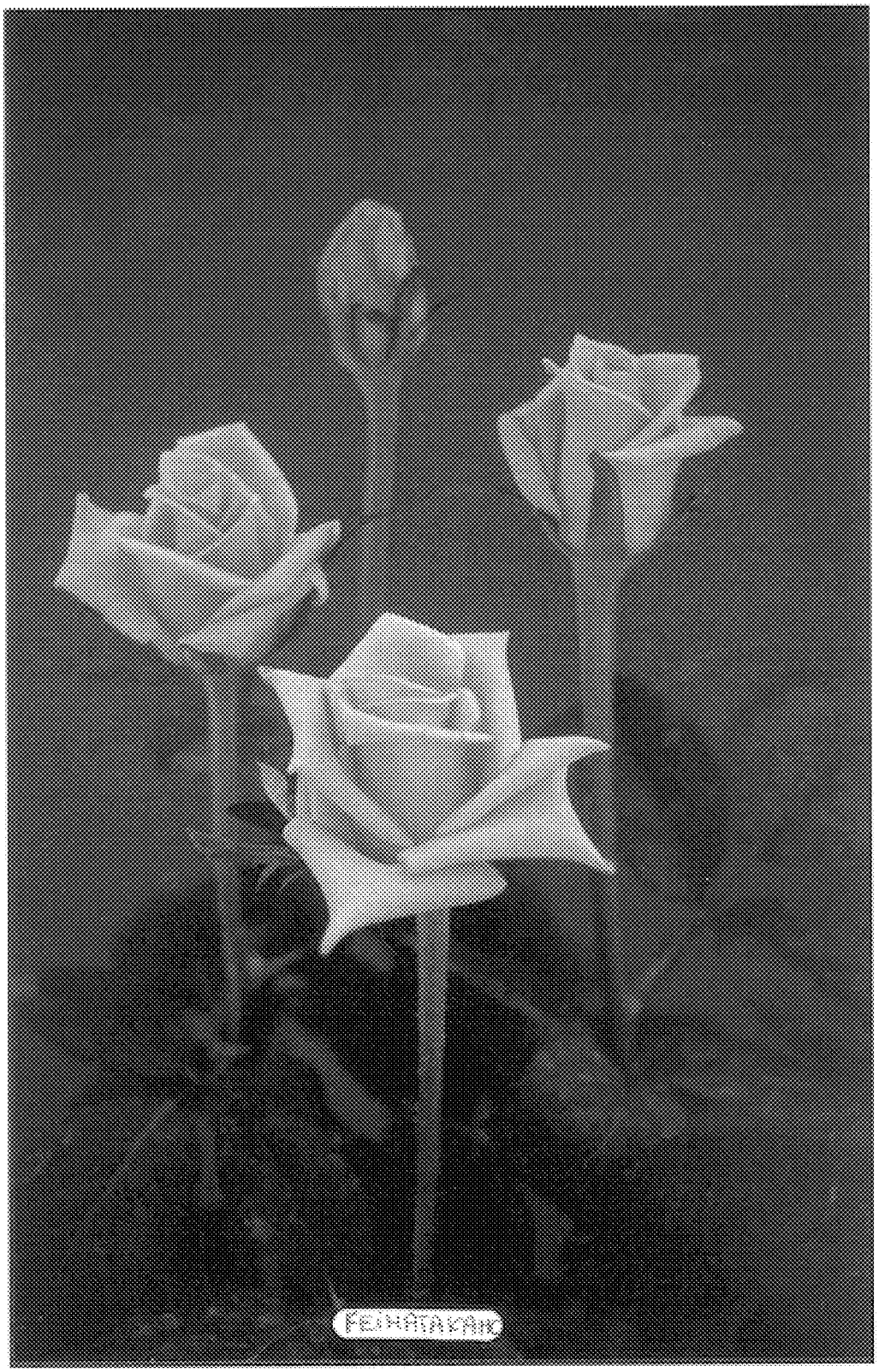
FELNHTAGNK